United States Patent [19]

Masciadri

[11] Patent Number: 5,162,577
[45] Date of Patent: Nov. 10, 1992

[54] PROCESS FOR LITHIATION OF 1,3-BIS(TRIFLUOROMETHYL)BENZENE

[75] Inventor: Raffaello Masciadri, Basel, Switzerland

[73] Assignee: Hoffmann-La Roche Inc., Nutley, N.J.

[21] Appl. No.: 649,089

[22] Filed: Feb. 1, 1991

[30] Foreign Application Priority Data

Feb. 13, 1990 [CH] Switzerland .................. 463/90

[51] Int. Cl.$^5$ .................. C07C 51/15; C07C 45/00
[52] U.S. Cl. .................. 562/493; 562/436; 568/436; 568/437; 568/438; 570/144; 570/191
[58] Field of Search .................. 568/436, 438, 437; 570/182, 183, 184, 185, 189, 206, 144, 191; 562/436, 493, 423

[56] References Cited

U.S. PATENT DOCUMENTS

| | | | |
|---|---|---|---|
| 3,632,658 | 1/1972 | Halasa | 570/206 |
| 3,663,585 | 5/1972 | Langer, Jr. | 260/439 |
| 3,751,491 | 8/1973 | Houlihan | 562/493 |
| 3,944,598 | 3/1976 | Pausian et al. | 562/493 |
| 3,985,799 | 10/1976 | Houlihan | 568/436 |

FOREIGN PATENT DOCUMENTS

| | | | |
|---|---|---|---|
| 1499563 | 10/1966 | France. | |
| 826619 | 1/1960 | United Kingdom | 562/493 |
| 1080167 | 6/1963 | United Kingdom. | |

OTHER PUBLICATIONS

Aeberli et al., "J. Organomet. Chem." vol. 67, pp. 321-325(1974).
Colemann et al., "J. Chem Soc., Perkin 11", vol. 1973.
Kodaira et al., "Bull. Chem. Soc. Japan" vol. 61, No. 4 (1988) pp. 1625-1631.
Grocock et al., J. Chem. Soc. (C), 3305-3308 (1971).
Brune et al., J. Organometallic Chem. 303:429-435 (1986).

*Primary Examiner*—Werren B. Lone
*Attorney, Agent, or Firm*—George M. Gould; William H. Epstein; Catherine R. Roseman

[57] ABSTRACT

A novel process for the lithiation of 1,3-bis(trifluoromethyl)benzene in a solvent is described, said process comprising carrying out the lithiation with the lithium salt of an amine of the general formula $$R^1R^2NH \qquad\qquad I$$

wherein $R^1$ and $R^2$ are secondary or tertiary lower alkyl or secondary or tertiary lower alkyl substituted by a lower alkyl or lower cycloalkyl or lower cycloaklyl substituted by a lower alkyl, or $R^1$ and $R^2$ taken together form a $C_{6-14}$-alkylene group in which the two carbon atoms linked with the nitrogen atom are secondary or tertiary and are separated from each other by 2 to 4 carbon atoms.

The solution of the lithiated 1,3-bis(trifluoromethyl)benzene obtained can be reacted with an electrophile which is suitable for the substitution of lethiated benzene derivatives, whereby a compound of the formula

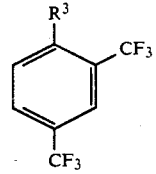

wherein $R^3$ signifies the residue of an electrophile which is suitable for the substitution of lithiated benzene derivatives, is obtained.

9 Claims, No Drawings

PROCESS FOR LITHIATION OF 1,3-BIS(TRIFLUOROMETHYL)BENZENE

BACKGROUND OF THE INVENTION

Compounds of the general formula

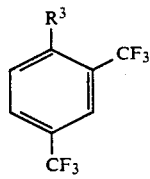
II wherein $R^3$ is a residue of an electrophile suitable for the substitution of lithiated benzene derivatives, are valuable intermediates which can be used for the manufacture of a wide variety of products. For example, they can be used for the manufacture of pharmaceutically active substances which have as a structural feature a 2,4-bis-(trifluoromethyl)phenyl group, e.g. for the manufacture of 4-[(Z)-2,4-bis(trifluoromethyl)styryl]-4,8-dimethyl-2,3-dioxabicyclo[3.3.1]nonan-7-one which is described in European Patent Publication No. 311 955 and which can be used for the prevention or control of malaria.

The lithiation of 1,3-bis(trifluoromethyl)benzene and the reaction of the solution obtained with electrophiles are known reactions. See K. Kodaira et al. in Bull. Chem. Soc. 61, 1625–1631 (1988) (document A), J. P. Coleman et al. in J. Chem. Soc. Perkin I 1973, 1903 et seq. (document B) and P. Aeberli et al. in J. Organomet. Chem. 67, 321–325 (1974) (document C). The lithiation of 1,3-bis(trifluoromethyl)benzene with n-butyllithium and the reaction of the solutions obtained with electrophiles, namely with elemental bromine or solid carbon dioxide, are described in these publications. The products obtained from these reactions are mixtures of bis(-trifluoromethyl)-bromobenzenes or, bis(trifluoromethyl)-benzoic acids, which consist essentially of the corresponding 2,4-isomers and of the corresponding 2,6-isomers, i.e. the lithiation and the subsequent reaction with the electrophiles takes place mainly in the 2-position and in the 4-position of the 1,3-bis(trifluoromethyl)benzene. Table I gives the compositions of the mixtures obtained from the reactions described in these publications.

TABLE I

| | | | Amount of isomers in % | | |
|---|---|---|---|---|---|
| Document | Electrophile | $R^3$ | 2,4-isomer | 2,6-isomer | other isomers |
| Document A | Br$_2$ | Br | 47.5 | 45.1 | 7.4 |
| Document A | " | " | 47.3 | 42.4 | 10.3 |
| Document B | CO$_2$ solid | —COOH | 56.3 | 35.0 | 8.7 |
| Document C | " | " | 60.0 | 40.0 | — |
| Document C | " | " | 62.0 | 38.0 | — |
| Document C | " | " | 59.0 | 41.0 | — |

As can be concluded from this Table, the ratio of 2,4-isomer to 2,6-isomer in the products obtained varies between about 1:1 and 3:2 in favour of the 2,4-isomers.

SUMMARY OF THE INVENTION

It has now surprisingly been found that the amount of 2,4-isomer in the products obtained can be increased dramatically when the lithium salt of an amine of the formula $R^1R^2NH$, wherein $R^1$ and $R^2$ each signify a secondary or tertiary lower alkyl or a secondary or tertiary lower alkyl substituted by a lower alkyl or a lower cycloalkyl, or a lower cycloalkyl substituted by a lower alkyl, or $R^1$ and $R^2$ taken together form a $C_6$–$C_{14}$-alkylene group in which the two carbon atoms linked with the nitrogen atom are secondary or tertiary and are separated from each other by 2 to 4 carbon atoms is used for the lithiation (see Table III at the end of the experimental section). By means of the process described herein there are obtained products in which the ratio of 2,4-isomer to 2,6-isomer varies from 4:1 to more than 100:1. The dramatic shift in the ratio in favour of the 2,4-isomers, enormously facilitates their separation from the isomer mixtures and their purification.

The present invention is concerned with a process for the lithiation of 1,3-bis(trifluoromethyl)benzene in a solvent which is suitable for this purpose, which process comprises carrying out the lithiation with the lithium salt of an amine of the general formula $R^1R^2NH$      I wherein $R^1$ and $R^2$ are secondary or tertiary lower alkyl or secondary or tertiary lower alkyl substituted by a lower alkyl, or lower cycloalkyl or lower cycloalkyl substituted by a lower alkyl, or $R^1$ and $R^2$ taken together form a $C_{6-14}$-alkylene group in which the two carbon atoms linked with the nitrogen atom are secondary or tertiary and are separated from each other by 2 to 4 carbon atoms.

In a further aspect the present invention is concerned with a process for the manufacture of compounds of the general formula

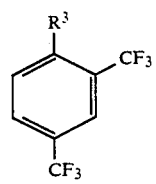
II wherein $R^3$ is the residue of an electrophile which is suitable for the substitution of lithiated benzene derivatives, which process comprises reacting the solution of the lithium salt of 1,3-bis(tri-fluoromethyl)benzene with an electrophile wherein said lithium salt is obtained by treating 1,3-bis(tri-fluoromethyl)benzene with a lithium salt of an amine of the formula $R^1R^2NH$      I wherein $R^1$ and $R^2$ are secondary or tertiary lower alkyl or secondary or tertiary lower alkyl substituted by a lower alkyl or lower cycloalkyl or lower cycloalkyl substituted by a lower alkyl, or $R^1$ and $R^2$ taken together form a $C_{6-14}$-alkylene group in which the two carbon atoms linked with the nitrogen atom are secondary or tertiary and are separated from each other by 2 to 4 carbon atoms.

A further object of the present invention is the use of lithium salts of amines of formula I above in the lithiation of 1,3-bis(trifluoromethyl)benzene.

DETAILED DESCRIPTION OF THE INVENTION

The object of the subject invention is the lithiation of 1,3-bis(trifluoromethyl)benzene in a solvent, which process comprises carrying out the lithiation with the lithium salt of an amine of Formula I. This invention includes the solution containing lithiated 1,3-bis(trifluoromethyl)benzene resulting from this process.

Lithiation in accordance with the invention is preferably carried out in a suitable conventional solvent such as lower open-chain or cyclic ether or mixtures thereof with an open-chain or cyclic lower hydrocarbon. The reaction temperature preferably lies in a range of about −80° C. to about room temperature, but preferably below 0° C. The preferred lithiating agents are the lithium salt of 2,2,6,6-tetramethylpiperidine, diisopropylamine, t-butylisopropylamine, di-t-butylamine, t-butylcyclohexylamine or dicyclohexylamine, especially the lithium salt of 2,2,6,6-tetramethyl-piperidine.

For the manufacture of compounds of Formula II, the solution of the lithiated 1,3-bis(trifluoromethyl)benzene obtained in accordance with the invention can be added to the electrophile or the electrophile can be added, preferably as rapidly as possible, to the solution of the lithiated 1,3-bis(trifluoromethyl)benzene obtained in accordance with the invention.

In an especially preferred embodiment elemental halogen, solid carbon dioxide, N,N-dimethylformamide or methyl iodide is used as the electrophile and a compound of formula II in which $R^3$ is bromine (when bromine is the halogen used), carboxy (when solid $CO_2$ is used), formyl (when N,N dimethylformamide is used), or methyl (when methyl iodide is used) is isolated as the product. In a particularly preferred embodiment solid carbon dioxide or N,N-dimethylformamide is used as the electrophile and 2,4bis(trifluoromethyl)benzoic acid (when $CO_2$ is used), or 2,4bis(trifluoromethyl)benzaldehyde (when N,N-dimethylformamide is used) is isolated as the product.

The term "lower" used in the present description denotes residues and compounds with a maximum of 7, preferably with a maximum of 4, carbon atoms. The term "alkyl" denotes straight-chain or branched, saturated hydrocarbon residues such as methyl, ethyl, propyl, isopropyl and t-butyl. The term "cycloalkyl" denotes cyclic, saturated hydrocarbon residues such as cyclopentyl and cyclohexyl.

The term "electrophile" denotes compounds which are capable of reacting with lithiated benzene derivatives in the sense of an addition or substitution. In accordance with this invention, any conventional electrophile may be used. Suitable electrophiles are, for example, the halogens bromine and iodine, nonenolizable, i.e. aromatic or α, β-unsaturated, aldehydes and ketones, N,N-di(lower alkyl)amides and cyclic N-formyl- and N-(lower alkanoyl)amines, carbon dioxide and lower alkyl halides.

The following Examples illustrate the present invention in more detail. However, they are not intended to limit its scope in any manner. All temperatures are given in degrees Celsius.

EXAMPLE 1

Lithiation of 1,3-bis(trifluoromethyl)benzene 27.2 ml (0.16 mol) of 2,2,6,6-tetramethylpiperidine are dissolved in 400 ml of tetrahydrofuran and this solution is cooled to −40° under a stream of argon. Then, 100 ml of a 1.6M solution of n-butyllithium in hexane are added thereto at −40° over a period of 10 minutes. The yellowish solution is warmed briefly to 0° with a water bath, then cooled to −75° and 20.2 ml (0.13 mol) of 1,3-bis(trifluoromethyl)benzene are added dropwise thereto at −75° over a period of 15 minutes. The violet solution obtained is stirred at −75° for a further hour.

Reaction of lithiated 1,3-bis(trifluoromethyl)benzene with electrophiles

At least 0.16 mol of the electrophile is added as rapidly as possible to the above violet solution at −75°. The solution warms by 10°–30° as a consequence of the exothermic reaction. The reaction mixture is then left to warm to 0° and subsequently poured slowly while stirring into 500 ml of a cold 3M hydrochloric acid solution. The mixture is diluted with 300 ml of hexane and the aqueous phase is separated. The organic phase is extracted with 500 ml of cold 3M hydrochloric acid solution, washed neutral twice with 500 ml of saturated sodium chloride solution each time, dried over sodium sulphate and filtered, whereupon the solvent is distilled off. The crude product obtained is purified by crystallization or distillation over a suitable column.

The compounds described hereinafter were obtained by means of this process:

(a) 2,4-Bis(trifluoromethyl)benzoic acid

| | |
|---|---|
| Electrophile: | Excess solid carbon dioxide. |
| Yield: | 80%. |
| M.p. | 104°. |
| $^1$H-NMR(CDCl$_3$): | 7.95(d, 1H, J=8Hz); 8.07(s, 1H); 8.12(d, 1H, J=8Hz)ppm. |
| MS(EI)m/e: | 258(M$^+$), 241(M$^+$—OH), 213, 194, 163, 144. |

(b) 1-Methyl-2,4-bis(trifluoromethyl)benzene

| | |
|---|---|
| Electrophile: | Methyl iodide. |
| Yield: | 60%. |
| M.p. | 104°. |
| $^1$H-NMR(CDCl$_3$): | 2.56(s, 3H); 7.43(d, 1H, J=8Hz); 7.69(d, 1H, J=8Hz); 7.86 (s, 1H)ppm. |
| MS(EI)m/e: | 228(M$^+$), 209(M$^+$—F), 159(M$^+$—CF$_3$). |

(c) 1-(Trimethylsilyl)-2,4-bis(trifluoromethyl)benzene

| | |
|---|---|
| Electrophile: | Trimethylchlorosilane. |
| Yield: | 65%. |
| B.p. | 75°/1.47kPa. |
| $^1$H-NMR(CDCl$_3$): | 0.373; 0.377; 0.382(3xs, 9H); 7.74(d, 1H, J=7.8Hz); 7.86(d, 1H, J=7.8Hz); 7.92(s, 1H)ppm. |
| MS(EI)m/e: | 271(M$^+$—CH$_3$), 267(M$^+$—F), 231, 151. |

(d) 2,4-Bis(trifluoromethyl)benzaldehyde

| | |
|---|---|
| Electrophile: | N,N-Dimethylformamide. |
| Yield: | 30%. |
| B.p. | 65°/1.47kPa. |
| $^1$H-NMR(CDCl$_3$): | 7.99(d, 1H, J=8.1Hz); 8.05(s, 1H); 8.27(d, 1H, J=8.1Hz); 10.44(m, 1H)ppm. |
| MS(EI)m/e: | 242(M$^+$), 241(M$^+$—H), |

-continued

223(M⁺—F), 222(M⁺—HF),
213(M⁺—CHO),
195, 194, 164, 163, 145, 144.

(e) 1-Bromo-2,4-bis(trifluoromethyl)benzene

| Electrophile: | Bromine. |
|---|---|
| Yield: | 43%. |
| B.p. | 95°/10kPa. |
| $^1$H-NMR(CDCl$_3$): | 7.66(dd, 1H, $J_1$=8.4Hz, $J_2$=2Hz); |
| | 7.88(d, 1H, $J_1$=8.4Hz); |
| | 7,94(d, 1H, $J_2$=2Hz)ppm. |
| MS(EI)m/e: | 294(M⁺), 292(M⁺), 273(M⁺—F), |
| | 213(M⁺—Br). |

EXAMPLE 2

With Temperature Variation

A solution of y mol of 2,2,6,6-tetramethylpiperidine in 400 ml of anhydrous tetrahydrofuran is cooled under a stream of argon to t° and there is added dropwise thereto at this temperature within 30 minutes 100·y/0.16 ml of a 1.6M solution of n-butyllithium in hexane. Subsequently, 20.2 ml (0.13 mol) of 1,3-bis(trifluoromethyl)-benzene are added dropwise thereto at t° within 15 minutes, the wine-red solution obtained is stirred for a further X minutes at t° and then at this temperature 20 ml (0.26 mol) of N,N-dimethylformamide are allowed to flow in rapidly from a dropping funnel. The internal temperature t rises by about 15° as a consequence of the exothermic reaction. The dark red solution obtained is then slowly added dropwise and while stirring and cooling to 500 ml of cold 3M hydrochloric acid (strongly exothermic). The emulsion obtained is diluted with 300 ml of hexane, the aqueous phase is separated, the organic phase is extracted with 500 ml of cold 3M hydrochloric acid, washed neutral twice with 250 ml of saturated sodium chloride solution each time, dried over sodium sulphate and the organic solvent is largely distilled off at 40° bath temperature/20 kPa. The residue is distilled over a column having a length of 20 cm, whereby firstly residual solvent is removed at 50° bath temperature/20 kPa and then the bath temperature is increased to 80° and the vacuum is increased to 1.4 kPa. During the increase in the internal temperature a forerun of about 1 g is removed and then the 2,4-bis(trifluoromethyl)benzaldehyde obtained distils over at 56°./1.4 kPa as a colourless liquid.

Results

TABLE II

| Reaction temperature t | Reaction time x | Amount of base y | Yield | Purity (GC) |
|---|---|---|---|---|
| −30° | 20 min. | 0.16 mol. (27.2 ml) | 70% | 98% |
| −20° | 15 min. | 0.16 mol (27.2 ml) | 70% | 98% |
| −10° | 3 min. | 0.16 mol (27.2 ml) | 70% | 98% |
| −10° | 5 min. | 0.13 mol (22.1 ml) | 70% | 96% |

$^1$H-NMR (CDCl$_3$): 7.99 (d,1H,J=8.1 Hz); 8.05 (s,1H); 8.27 (d,1H,J=8.1 Hz); 10.44 (m,1H) ppm.

MS, peaks at m/e: 242 (M⁺), 241 (M⁺-H), 223 (M⁺-F), 222 (M⁺-HF), 213 (M⁺-CHO), 195, 194, 164, 163, 145, 144.

EXAMPLE 3 a) A solution of 68 ml (0.4 mol) of 2,2,6,6-tetramethylpiperidine in 1 l of tetrahydrofuran is cooled under argon to −10° and at this temperature there are added dropwise thereto while stirring 250 ml of a 1.6M solution of n-butyllithium in hexane. Subsequently, 62 ml (0.4 mol) of 1,3-bis(trifluoromethyl)-benzene are added dropwise thereto at −10° within 5 minutes. The resulting wine-red solution is stirred at −10° for a further 5 minutes and then 62 ml (0.8 mol) of N,N-dimethylformamide are allowed to flow in rapidly. The internal temperature rises by 15° as a consequence of the exothermic reaction. The dark brown solution obtained is then added slowly and under a slight argon pressure to 1.2 l of stirred, ice-cold 1M hydrochloric acid. The internal temperature rises to 10° as a consequence of the stongly exothermic reaction in spite of constant cooling. The resulting emulsion is diluted with 750 ml of hexane, the aqueous phase (1.5 l) is separated and stored for the recovery of 2,2,6,6-tetra- methylpiperidine. The organic phase (1.9 l) is extracted twice with 1 l of water each time, dried over sodium sulphate, filtered and the organic solvent is distilled off at 40° under a vacuum (20 kPa). The residue (about 100 ml) is distilled over a column having a length of 20 cm, firstly at 50° bath temperature under a vacuum of 20 kPa in order to remove the residual solvent, then the bath temperature is increased to 80° and the vacuum is increased to 1.4 kPa. A forerun is removed until the constant internal temperature of 57° has been reached and then the residue distils over as a fraction at 57°/1.4 kPa. There are obtained 68 g (70%) of 2,4-bis(trifluoromethyl)benzaldehyde with a purity (GC) of 96-98%.

(b) Recovery of 2,2,6,6-tetramethylpiperidine

The above stored acidic aqueous phase (1.5 l) is extracted once with 1 l of diethyl ether, cooled to 10°, 200 ml of crude 28 percent sodium hydroxide solution are added thereto while stirring and cooling and the mixture is saturated with sodium chloride. The basic solution obtained is extracted once with 1.5 l of diethyl ether, the organic phase is dried over sodium sulphate, filtered and the ether is distilled off at 40° in a vacuum (70 kPa). The residue (about 200 ml) is distilled at normal pressure over a column having a length of 20 cm, whereby the residual solvent (40°-110° C.), a forerun (110°-150°) and finally 53 g (94%) of 2,2,6,6-tetramethylpiperidine (155°) with a purity (GC) of 94-99% distil over.

EXAMPLE 4

A solution of 100 ml (0.21 mol) of lithium diisopropylamide in tetrahydrofuran is cooled under argon to −70° and at this temperature there are added dropwise thereto while stirring 31 ml (0.2 mol) of 1,3-bis(trifluoromethyl)benzene. The resulting dark red, viscous suspension is stirred at −70° for a further 30 minutes and then 31 ml (0.4 mol) of N,N-dimethylformamide are allowed to flow in rapidly. The internal temperature rises to −20° as a consequence of the exothermic reaction in spite of continuous cooling. The violet solution obtained is then processed further as described in Example 3a). 2,4-Bis(trifluoromethyl)-benzaldehyde is obtained.

TABLE III

Gas chromatographical analysis of the crude products containing the respective compound of formula II:

| Example | Electrophile | $R^3$ | 2,4-isomer | 2,6-isomer | other isomers |
|---|---|---|---|---|---|
| 1e) | $Br_2$ | Br | 79.7 | 20.3 | — |
| 1a) | $CO_2$ solid | —COOH | >90 | <10 | — |
| 1b) | $CH_3$—I | —$CH_3$ | 92.2 | 6.5 | 1.3 |
| 1c) | $ClSi(CH_3)_3$ | —$Si(CH_3)_3$ | 90.8 | 8.1 | 1.1 |
| 1d) | DMF | —CHO | 93.1 | 6.9 | — |
| 2 (−30°) | " | " | 98.1 | 0.7 | 1.2 |
| 2 (−20°) | " | " | 98.6 | 0.5 | 0.9 |
| 2 (−10°) | " | " | 98.1 | 0.8 | 1.1 |
| 3a) | " | " | 98.4 | 0.8 | 0.8 |
| 4 | " | " | 34.0 | <1.0 | <1.0 |

DMF = N,N-Dimethylformamide

I claim:

1. A process for the lithiation of 1,3-bis(tri-fluoromethyl)benzene which process comprises treating the 1,3-bis(tri-fluoromethyl)benzene in a solvent with the lithium salt of an amine of the formula $$R^1R^2NH \qquad I$$

wherein $R^1$ and $R^2$ are secondary or tertiary lower alkyl or secondary or tertiary lower alkyl substituted by a lower alkyl, or lower cycloalkyl or lower cycloalkyl substituted by a lower alkyl, or $R^1$ and $R^2$ taken together form a $C_{6-14}$-alkylene group in which the two carbon atoms linked with the nitrogen atom are secondary or tertiary and are separated from each other by 2 to 4 carbon atoms.

2. A process of claim 1, wherein the solvent is a lower open-chain or cyclic ether or a mixture thereof with an open-chain or cyclic lower hydrocarbon.

3. A process of claim 1, wherein the amine salt is 2,2,6,6-tetramethylpiperidine.

4. A process for the manufacture of compounds of the formula

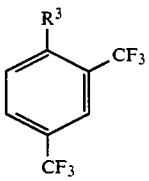

wherein R3 is the residue of an electrophile which is suitable for the substitution of lithiated benzene derivatives, which process comprises reacting the solution of the lithium salt of 1,3-bis(tri-fluoromethyl)benzene with an electrophile wherein said lithium salt is obtained by treating 1,3-bis(tri-fluoromethyl)benzene with a lithium salt of an amine of the formula $$R^1R^2NH \qquad I$$

wherein $R^1$ and $R^2$ are secondary or tertiary lower alkyl or secondary or tertiary lower alkyl substituted by a lower alkyl or lower cycloalkyl or lower cycloalkyl substituted by a lower alkyl, or $R^1$ and $R^2$ taken together form a $C_{6-14}$-alkylene group in which the two carbon atoms linked with the nitrogen atom are secondary or tertiary and are separated from each other by 2 to 4 carbon atoms.

5. A process of claim 4, wherein the electrophile is added, as rapidly as possible, to the solution of the lithiated 1,3-bis(trifluoromethyl)benzene.

6. A process of claim 4, wherein the solution of the lithiated 1,3-bis(trifluoromethyl)benzene is added to the electrophile.

7. A process of claim 4, wherein the electrophile is elemental bromine, solid carbon dioxide, N,N-dimethylformamide or methyl iodide and a compound of formula II in which $R^3$ signifies bromine, carboxy, formyl or methyl is isolated as the product.

8. A process of claim 7, wherein the electrophile is solid carbon dioxide and 2,4-bis(trifluoromethyl)-benzoic acid is isolated as the product.

9. A process of claim 7, wherein the electrophile is N,N-dimethylformamide and 2,4-bis-(trifluoromethyl)-benzaldehyde is isolated as the product.

* * * * *